United States Patent [19]

Etemad-Moghadam

[11] Patent Number: 5,407,675
[45] Date of Patent: Apr. 18, 1995

[54] METHOD AND COMPOSITION FOR USE ON THE SCALP AND EYEBROW REGION OF A SUBJECT

[76] Inventor: Parviz Etemad-Moghadam, 6 Aref-Nass St. Valiassar Ave., Shemiran, Islamic Rep. of Iran

[21] Appl. No.: 566,125

[22] Filed: Aug. 10, 1990

[51] Int. Cl.⁶ .................................................. A61K 6/00
[52] U.S. Cl. .................................... 424/401; 424/70.1; 424/74; 424/195.1; 424/537
[58] Field of Search .................... 424/70, 439, 401, 74, 424/537, 195.1; 514/23

[56] References Cited

U.S. PATENT DOCUMENTS

| | | | |
|---|---|---|---|
| 3,859,436 | 1/1975 | Jacobi | 514/23 |
| 4,670,255 | 6/1987 | Yoshizumi et al. | 424/70 |
| 4,886,665 | 12/1989 | Kovacs | 424/439 |
| 5,055,456 | 10/1991 | Harris et al. | 424/70 |

*Primary Examiner*—Thurman K. Page
*Assistant Examiner*—William E. Benston, Jr.
*Attorney, Agent, or Firm*—Basile and Hanlon

[57] ABSTRACT

A composition suitable for used on areas of the scalp and/or eyebrows in which hair loss is experienced and a method for applying the same. The composition includes a naturally occurring nutrient system such as naturally occurring honey, and a naturally occurring material capable as functioning as an epidermal stimulant such as an aqueous extract of leaves of *Urtica dioica* contained in a suitable carrier medium which is also, preferably compounded from naturally occurring products.

18 Claims, No Drawings

METHOD AND COMPOSITION FOR USE ON THE SCALP AND EYEBROW REGION OF A SUBJECT

BACKGROUND OF THE INVENTION

1. Field of the Invention

This invention relates to compositions and methods which may promote and maintain hair growth selectively in the scalp and eyebrow region of a subject. More specifically, this invention relates to compositions formulated for topical application on the specific region to be treated which are composed entirely of food-grade or naturally occurring components. Finally, this invention also relates to compositions which retard or reverse pigmentation loss in hair and hair follicle cells.

2. Background of the Related Art

Historically, many compositions have been advanced relating to the induction and stimulation of hair growth by the topical application of hair tonics and various preparations. With the exception of MINOXIDIL, none of these compositions has ever proven to be sufficiently effective whether administered topically, orally or systemically. Furthermore, these compositions are based on active ingredients which are synthetic in nature and which, generally, are classified as pharmaceutical drugs. Thus there is the danger of unwanted side effects, the necessity for medical monitoring etc. To date, no composition has been advanced which is effective in maintaining hair growth and promoting hair regrowth that is comprised of naturally occurring food-grade materials.

Thus, it would be desirable to develop a method and composition which promotes and maintains hair growth. It would also be desirable that this method and composition promote and maintain hair growth selectively only in scalp and eyebrow regions of the subject's skin. It would also be desirable that such a composition be topically applicable and composed of naturally occurring food-grade constituents.

SUMMARY OF THE INVENTION

The present invention is directed to a method and composition for promoting and maintaining hair growth in the scalp and eyebrow region of a subject. The composition consists essentially of an effective amount of a natural nutrient system such as naturally occurring honey; and effective amount of a naturally occurring topically active mild epidermal stimulant such as a concentrated solution of a steam extract of dried nettle leaves as well as a suitable carrier material.

The method set forth in the present invention comprises the steps of:
  topically applying a portion of the composition of the present invention to the scalp and/or eyebrow region of the subject after that region has been suitably cleansed;
  massaging the region to which the composition has been applied for an interval sufficient to mechanically stimulate blood flow in the region and permit penetration of the applied composition; and
  removing the applied composition after an interval sufficient to permit absorption of the composition by hair-and pigment- generating cells of the hair follicles.

DETAILED DESCRIPTION OF THE PREFERRED EMBODIMENT

The present invention is predicated upon the unexpected discovery that a composition consisting essentially of naturally occurring food-grade components can be effective in promoting and maintaining hair growth, thickness and color when topically applied to the scalp and/or eyebrow region of a subject.

The composition of the present invention maintains or regenerates hair growth selectively only in regions containing previously active hair generating cells which have become dormant such as on the scalp and eyebrow region of an individual. It has been found, quite unexpectedly, that application of the composition of the present invention to non-hair producing regions or regions producing only fine skin hair, i.e., epidermal regions outside the natural hair line of the subject does not result in unwanted follicle stimulation and hair growth. Furthermore, it has been found that systematic application of the composition of the present invention over a specified time period permits regrowth of pigmented hair in a large percentage of the subject tested.

Without being bound to any theory, it is believed that the natural nutrient system and the naturally occurring, topically active epidermal stimulant employed in the composition of the present invention serve to stimulate and nourish the follicle cells surrounding each hair. Once nourished and stimulated, many hair follicles which have remained dormant since the onset of baldness or hair loss are stimulated to produce a regrowth of hairs.

The composition of the present invention consists essentially of:
  an effective amount of a natural nutrient system consisting essentially of naturally occurring honey;
  an effective amount of a naturally occurring topically active stimulant derived from dried leaves of plants of the Urticcae genus; and
  a suitable carrier material optionally, the composition can also contain a naturally occurring nutritive moisturizing material such as vegetable oil selected from the group consisting of apricot oil, avocado oil, wheat germ oil, almond oil, coconut oil, sesame oil, corn oil, soya oil, and mixtures thereof.

The carrier material of the present invention is preferably composed of rose water and a suitable naturally occurring emulsifier. In the preferred embodiment the naturally occurring emulsifier is an admixture of bees wax and borax. The carrier can be formulated such that the composition of the present invention is a cream, ointment or spray. The carrier may optionally contain small amounts of materials which enhance the texture and appearance of the composition as desired, for example, glycerin.

The composition of the present invention contains an effective amount of a natural nutrient system. In the preferred embodiment, this system is naturally occurring honey. As defined herein, the term "naturally occurring honey" refers to pure honey produced by honey bees from naturally occurring flower nectar. Preferably, the honey employed is defined as "extra pure"; i.e., containing no other non-honey or non-naturally occurring constituents. Preferably, at least a portion of the honey employed in the present invention is of the type generally referred to as "royal jelly". Royal jelly is the part of the honey specifically formulated in the hive and fed to the queen bee. Royal jelly preferably comprises between about five and about fifty percent of the naturally occurring honey constituent of the composition of the present invention.

The composition of the present invention also includes a naturally occurring topically active mild epidermal stimulant such as that found in a concentrated solution of a steam extract of dried nettle leaves. The nettle leaves employed in the present invention are preferably those harvested from the plant *Urtica dioica*; colloquially referred to as "prickly nettle".

In preparing the steam extract employed in the present invention, mature nettle leaves are dried and finely pulverized. The resulting powder is steam-extracted to produce a viscous syrup extract. This can be accomplished by adding a volumetric portion of boiling water to an equal volumetric portion of nettle leaves. The material is, then, subjected to indirect heat for a period of two to ten hours. The resulting viscous syrup extract is then concentrated by evaporation to a level one half that of the initial syrup volume. The resulting concentrated extract can then be admixed with the natural nutrient system in the composition of the present invention.

Without being bound to any theory, it is hypothesized that the naturally occurring honey employed in the composition of the present invention provides a nutritive material necessary to, and desirable for, the cells of dormant hair follicles. The concentrated solution of the steam extract of dried nettle leaves is believed to have a stimulatory effect on the follicle cells and surrounding tissue. Thus, the amounts of both materials would be determined by the respective nutritive and stimulatory requirements of the follicle cells.

In the present invention, it is preferred that the extract of dried nettle leaves be present in an amount between about 0% and about 20% by total effective composition volume. The naturally occurring honey is present in an amount between about 1.0% and about 90.0% by total effective composition volume. Preferably the naturally occurring honey is present in an amount between about 1.0% and 75% by total effective composition al with an amount between about 3.0% and about 60% being most preferred.

The honey and nettle extract can be admixed with a naturally occurring, nutritive carrier material in amounts suitable to permit topical application of the composition. The carrier material may optionally include small amounts of texture and appearance-enhancing materials such as glycerin. When present, glycerin is present in amounts effective to achieve these objectives.

In the preferred embodiment, the carrier material consists essentially of an aqueous material such as rose water. The rose water is present in an amount suitable to form a spray, cream or lotion which contains an effective amount of the active ingredients. The term "rose water" as employed herein is defined as an aqueous material derived from the steam extraction of rose petals.

The amount of rose water preferably present in the composition of the present invention is generally dependent on the formulation requirements and manner in which the composition of the present invention is to be applied. Variations in the amount of rose water employed will result in a spray, cream, or an oil-based lotion. Such variations would be readily apparent to one reasonably skilled in the art.

The carrier material also generally comprises a suitable emulsion. In the preferred embodiment, borax or similar materials are employed in sufficient quantities to achieve a suitable emulsion.

Where a thicker consistency is desired, the carrier material may also contain bees wax. The amount of the bees' wax present in the carrier material would be sufficient to provide a composition having a consistency of an ointment or a cream. It is to be understood that other suitable carrier materials can be effectively employed in the composition of the present invention and are to be considered within the scope of this invention.

The preferred embodiment of the composition of the present invention also comprises a vegetable oil constituent. Without being bound to any theory, it is believed that this constituent provides additional nutritive and stimulative qualities to the composition as well as having a lubricating and moisturizing valve. The vegetable oil constituent is selected from the group consisting of apricot oil, avocado oil, wheat germ oil, almond oil, coconut oil, sesame oil, corn oil, soya oil, and mixtures thereof. The vegetable oil constituent is preferably present in the composition of the present invention in an amount between about 1.0 and about 80.0%, preferably in an amount between about 10% and about 80% by total effective composition. In the preferred embodiment, the composition of the present invention contains between about 6% and about 10% apricot oil, between about 4% and about 10% by volume avocado oil and between about 4% and about 10% wheat germ oil. The composition may further contain between about and about 15% almond oil, between about 9% and about 15% coconut oil, between about 19% and about 30% sesame oil, between about 4% and about 7% corn oil and between about 0.1 and about 0.3% soya oil. These amounts being stated as a percentage of total composition volume.

Without being bound to any theory, it is believed that the naturally occurring plant-derived oils employed in the present invention have dermatological utility in that they lubricate and moisturize the skin surface thereby eliminating dry skin and replacing naturally occurring oils which may be diminished in the affected bald regions. These naturally occurring oils exhibit nutritive and stimulatory effects when applied alone or in combination with honey and nettle extract.

The compositions of the present invention are particularly efficacious when treating forms of naturally occurring hair loss such as natural pattern baldness, and conventional pattern baldness. The compositions may also have utility in treating unnatural hair loss due to chemotherapy and other medical treatments.

In the method of the present invention, the above defined composition is preferably applied in the manner described subsequently.

Initially, the affected scalp or eyebrow region is thoroughly cleansed of dirt, oils and dead cells by a natural mildly acidic cleanser preferably having mild bacteriocidal or bacteriostatic and astringent properties. In the preferred embodiment, the natural mild cleanser is an aqueous solution containing naturally occurring, food-grade alcohols and naturally occurring food-grade pH lowering agent such as acetic acid. The cleansing solution employed in the method of the present invention is, preferably, an aqueous solution of rose water, cider vinegar, and ethanol. The cleansing solution preferably contains between about 2% and about 20% by volume food-grade ethanol, sufficient cider vinegar to provide a solution pH between about 4 and about 6.5, preferably between about 4.5 and about 5.5, with the balance being rose water.

Once the treatment region is cleansed, the composition of the present invention can then be topically applied to the affected region while massaging along two perpendicular directions for an interval sufficient to mechanically enhance blood circulation in the dermis and to permit the composition to penetrate into the affected region; preferably for a period between about two to about fifteen minutes. The amount of composition applied is determined by the area to be treated. In general, it is preferred that liberal amounts of the material be applied such that a slight excess of the composition of the present invention remains on the affected region after massage.

Once the composition of the present invention is applied, it is permitted to remain on the affected region for a period between about two and about ten hours, preferably overnight while the subject sleeps. After this interval, it is rinsed off using any commercially available natural, non-medicated shampoo.

The composition is reapplied at a frequency of two to four times per week without interruption for an interval of three to six months or until hair growth and/or regrowth is evidenced. After sufficient hair growth and/or regrowth is evidenced, the frequency of applications can be gradually reduced.

It is to be understood that other combinations of the above-listed and described ingredients can be employed in the method of the present invention in which one of the enumerated components is omitted. Without being bound to any theory, it is believed that the vegetable oils discussed previously provide both nutritive and stimulatory effects. Because of this it is possible, while not preferred to formulate compositions in which the nettle syrup extract and/or the honey component are omitted. These compositions will provide at least a portion of the salutary effects found in the preferred embodiment and will provide a composition which could be used in very early hair loss situations.

In order to more clearly illustrate the composition and method of the present invention, the following examples are set forth. These examples are included for illustrative purposes only and are not to be construed as limitative of the present invention.

EXAMPLE 1

A composition according to the present invention was prepared by heating and admixing the oils and bees wax in the amounts set forth in Table 1. The portions of honey, rose water and bees wax were admixed and gently heated to a temperature below the boiling point of the solution in a separate container until the borax was thoroughly dissolved. The rose water solution was then gently added and admixed into the bees wax/oil material with continuous and thorough stirring during the addition. Once addition was completed, the resulting material was gently cooled with continuous mixing until a homogenous soft moisturizing cream was obtained. The resulting cream was then placed in containers and stored until use.

EXAMPLE 2

A male middle-aged subject, whose total scalp, with the exception of a ring circulating the lower sides and rear, was exposed to alopecia (baldness) for over twenty years and reported no evidence of any hair regrowth during the twenty-year period, applied the composition of Example 1 three times per week. Each application was accompanied by a fifteen minute massage of the effected region. Hair regrowth and maintenance was reported after six months of application. After this period, the effected region was examined. Short hair was found to abundantly cover the once completely bald area of the scalp. In addition, numerous long, thick, and pigmented hairs were observed throughout the scalp and in the crown.

EXAMPLE 3

A young man with advanced signs of baldness at an early age, applied the composition set forth in Example 1 in the manner directed in Example 2. Prior to treatment, the subject had reported no evidence of spontaneous remission of symptoms. Shortly after the outset of treatment, regrowth of visible and abundant hair on the scalp was evidenced. Increases in thickness and length the hair was evidenced and well maintained after six months of application.

EXAMPLE 4

A seventy-six year old woman affected by diffuse hair loss and rarefication of hair throughout the scalp as well as depletion of hair in the front, employed the composition as set forth in Examples 1 and 2. The subject experienced cessation of hair loss within six weeks of the start of the treatment while experiencing regrowth of hair within eight months. At that time, the affected area was examined. Short and pigmented hair was found to abundantly cover the affected areas.

EXAMPLE 5

An old man of seventy years of age with completely white hair employed the composition set forth in Examples 1 and 2. Abundant regrowth of highly pigmented black hair was experienced in the affected region of the scalp four months after the start of the treatment.

EXAMPLE 6

Three woman volunteers have applied the invented composition to their eyebrows in the manner described in Examples 1 and 2. Cessation of eyebrow hair loss and a notable increase in the density of their eyebrows were observed within a short interval after the commencement of treatment.

EXAMPLE 7

A composition formulated according to the present invention is formulated in the manner set forth in Example 1. All components are employed in the amounts listed in Table I with the exception that the nettle syrup extract and the vegetable oils are omitted completely; yielding a composition of naturally occurring honey, glycerin, rose water, extra pure bees wax, and borax. The resulting material is tested on several subjects exhibiting varying degrees of hair loss. The manner of application is outlined in Example 2. An arrested or slowed rate of hair loss is evidenced in most instances within one year. In some instances, regrowth is evidenced in that interval.

EXAMPLE 8

A composition according to the present invention is formulated in the manner set forth in Example 1. All components are employed in the amounts listed in Table I with the exception of nettle syrup concentrate which is omitted completely. The resulting material is tested on several subjects exhibiting varying degrees of hair loss. The manner of application is outlined in Example 2. An arrested or slowed rate of hair loss is evidenced in most instances within six to eight months. In some instances, regrowth is evidenced in that interval.

TABLE I

| Ingredients | Volume (cc) |
| --- | --- |
| Melted Extra Pure Honey | 4.9 |
| Nettle Syrup Concentrate | 2.5 |
| Apricot Oil | 6.9 |
| Avocado Oil | 4.9 |
| Wheat Germ Oil | 4.9 |
| Almond Oil | 9.9 |
| Coconut Oil | 9.9 |
| Sesame Oil | 19.7 |
| Corn Oil | 4.9 |
| Soya Oil | 1.8 |
| Glycerin | 4.9 |
| Rose Water | 26.8 |
| Extra Pure Bees Wax | 14.0 gm |
| Borax | 1.2 gm |

What is claimed is:

1. A topically applied, self-contained composition for the scalp and eyebrow region of a subject consisting essentially of:
   an effective amount of a natural nutrient material consisting essentially of naturally occurring honey;
   an effective amount of a naturally derived topically active stimulant consisting essentially of extracts derived from *Uritica dioica;*
   a moisturizer/lubricant constituent consisting of a vegetable oil selected from the group consisting of almond oil, coconut oil, sesame oil, corn oil, soya oil, and mixtures thereof; and
   a suitable carrier material.

2. The composition of claim 1 wherein the topically active stimulant is obtained by extraction of finely powdered dried leaves of *Urtica dioica* by an equal volume of water, the resulting extract being concentrated to one half of its original volume by evaporation.

3. The composition of claim 2 wherein the obtained extract is present in an amount between about 0.1% and about 20.0% by volume and the naturally occurring honey is present in an amount between about 1.0% and about 90.0% by volume.

4. A topically applied, self-containing composition for the scalp and eyebrow region of a subject consisting essentially of:
   an effective amount of a natural nutrient material useful to dormant hair follicle cells consisting essentially of naturally occurring honey;
   an effective amount of a naturally derived topically active stimulant consisting essentially of extracts derived from *Uritica dioica;*
   a suitable carrier material; and
   a moisturizer/lubricant constituent selected from the group consisting of apricot oil, avocado oil, wheat germ oil, almond oil, coconut oil, sesame oil, corn oil, soya oil, and mixtures thereof, the moisturizer/lubricant constituent present in an amount between about 10.0% and about 80.0% by total composition volume.

5. The composition of claim 3 wherein the moisturizer/lubricant constituent specifically comprises between about 6% volume and about 10% volume apricot oil, between about 4% volume and about 10% voluem avocado oil and between about 4% volume, about 10% volume wheat germ oil and mixtures thereof.

6. The composition of claim 4 wherein the moisturizer/lubricant constituent specifically comprises between about 9% volume and about 15% volume almond oil, between about 9% volume and about 15% volume coconut oil, between about 19% volume and about 30% volume sesame oil, between about 4% and about 7.0% volume corn oil, and between about 1.0% volume and about 3.0% volume soya oil.

7. The composition of claim 3 wherein the carrier material consists essentially of:
   rose water;
   bees wax admixed with the rose water in an amount sufficient to provide a cream consistency; and
   an emulsifier present in an amount sufficient to maintain the composition components in a stable emulsion.

8. The composition of claim 4 wherein the carrier material specifically comprises:
   glycerin;
   rose water;
   bees wax admixed with the rose water in an amount sufficient to provide a cream consistency; and
   an emulsifier present in an amount sufficient to maintain the composition components in a stable emulsion.

9. A topically applied, self-contained composition for the scalp and eyebrow region of a subject consisting essentially of:
   an effective amount of natural nutrient system consisting essentially of naturally occurring honey;
   a moisturizer/lubricant constituent selected from the group consisting of apricot oil, avocado oil, wheat germ oil, almond oil, coconut oil, sesame oil, corn oil, soya oil and mixtures thereof; and
   a carrier material consisting essentially of:
   rose water;
   bees wax admixed in the rose water in an amount sufficient to provide the resulting admixture with a cream consistency; and
   an emulsifier present in an amount sufficient to maintain the composition components in a stable emulsion.

10. The composition of claim 1 wherein the carrier material consists essentially of:
    rose water;
    bees wax admixed with the rose water in an amount sufficient to provide a cream consistency; and
    an emulsifier present in an amount sufficient to maintain the composition components in a stable emulsion.

11. The composition of claim 9 wherein the natural nurient system consisting essentially of honey is present in an amount between about 1.0 and about 50.5% by total composition volume.

12. A topically applied, self-contained composition for the scalp and eyebrow region of a subject, the composition consisting essentially of:
    naturally occurring honey present in an amount between about 3.0% and about 75% by total composition volume;
    a concentrated aqueous solution of an extract of leaves of *Urtica dioica* present in an amount between about 1.0% and about 20 by total composition volume;
    a moisturizer/lubricant constituent present in an amount between about 2.0% and about 10.0% by total composition volume, the moisturizer/lubricant constituent selected from the group consisting of apricot oil, avocado oil, wheat germ oil, almond oil, coconut oil, sesame oil, corn oil, soya oil and mixtures thereof; and a suitable carrier material.

13. A topical method for promoting general overall health of the scalp and eyebrow region of a subject, the method comprising the steps of:

topically applying a portion of the composition of claim 3 to the scalp and/or eyebrow region;

massaging the region to which the composition has been applied for an interval sufficient to stimulate blow flow in the region and permit penetration of the applied composition; and permitting the composition to remain on the region for an interval sufficient to permit uptake of a portion of the composition by hair follicile cells in the associated region.

14. The method of claim 13 wherein the uptake interval is between about two and about ten hours.

15. The method of claim 13 further comprising the step of cleansing the region to which the composition is to be applied prior to the topical application step.

16. The method of claim 13 wherein the cleansing step is accomplished by the application of a cleansing solution consisting essentially of an aqueous admixture of cider vinegar, food-grade alcohol, and rose water.

17. A topically applied, self-contained composition for the scalp and eyebrow region of a subject consisting essentially of:

a natural nutrient system consisting essentially of naturally occurring honey present in an amount between about 1.0 and about 90.0 by total composition volume;

a naturally derived topically active stimulant consisting essentially of a aqueous extract derived from leaves of plants of the Urticcae genus present in an amount from about 1.0 to about 20.0% by total composition volume;

a moisturizer/lubricant constituent selected from the group consisting of apricot oil, avocado oil, wheat germ oil, almond oil, coconut oil, sesame oil, corn oil, soya oil, and mixtures thereof; and a suitable carrier material.

18. The method of claim 12 wherein the material consists essentially of:

rose water;

bees wax admixed with the rose water in an amount sufficient to provide a cream consistency; and an emulsifier present in an amount sufficient to maintain the composition components in a stable emulsion.

* * * * *